(12) United States Patent
Ingallina et al.

(10) Patent No.: US 6,531,638 B2
(45) Date of Patent: Mar. 11, 2003

(54) PROCESS FOR THE PREPARATION OF CATALYTIC SYSTEMS FOR THE OXIDATIVE DEHYDROGENATION OF ALKYLAROMATICS OR PARAFFINS

(75) Inventors: Patrizia Ingallina, San Donato Milanese (IT); Luciano Carluccio, San Donato Milanese (IT); Carlo Perego, Carnate (IT); Gastone Del Piero, Milan (IT); Fabio Assandri, Piadena (IT)

(73) Assignees: Enichem S.p.A., San Donato Milanese (IT); Enitecnologie S.p.A., San Donato Milanese (IT)

( * ) Notice: Subject to any disclaimer, the term of this patent is extended or adjusted under 35 U.S.C. 154(b) by 0 days.

(21) Appl. No.: 09/870,655

(22) Filed: Jun. 1, 2001

(65) Prior Publication Data

US 2002/0025908 A1 Feb. 28, 2002

(30) Foreign Application Priority Data

Jun. 1, 2000 (IT) ...................................... MI2000A1220

(51) Int. Cl.$^7$ ........................... B01J 21/10; B01J 23/16; B01J 23/20; C07C 4/06; C07C 5/333
(52) U.S. Cl. ...................... 585/444; 585/661; 502/340; 502/353
(58) Field of Search ................................ 502/340, 353; 585/444, 661

(56) References Cited

U.S. PATENT DOCUMENTS

| | | | |
|---|---|---|---|
| 3,318,966 A | 5/1967 | Capp et al. | |
| 4,444,908 A | 4/1984 | Hass et al. | |
| 5,043,309 A | * 8/1991 | Najjar et al. | 502/340 |
| 6,228,798 B1 | * 5/2001 | Sookraj | 502/209 |

FOREIGN PATENT DOCUMENTS

| | | |
|---|---|---|
| EP | 0 482 276 | 4/1992 |
| EP | 1 057 530 | 12/2000 |

* cited by examiner

*Primary Examiner*—Tom Dunn
*Assistant Examiner*—Christina Ildebrando
(74) *Attorney, Agent, or Firm*—Oblon, Spivak, McClelland, Maier & Neustadt, P.C.

(57) ABSTRACT

Process for preparing catalytic systems consisting of:
 a vanadium oxide;
 a bismuth oxide;
 and a carrier consisting of magnesium oxide, comprising:
  preparing of solutions based on derivatives of the components of the catalytic system;
  mixing the solutions and optional aging;
  drying the solution;
  first heating, in the presence of air, of the solid obtained from the drying at a temperature ranging from room value to a temperature of between 290 and 310° C., for a time ranging from 1 to 3 hours;
  additional heating, in the presence of air, of the solid for a time ranging from 2 to 4 hours at the calcination temperature ranging from 600 to 850° C.;
  calcination, in the presence of air, of the solid at a constant temperature, ranging from 600 to 850° C., reached in the additional heating, for a time ranging from 8 to 16 hours.

14 Claims, 10 Drawing Sheets

Figure 1:
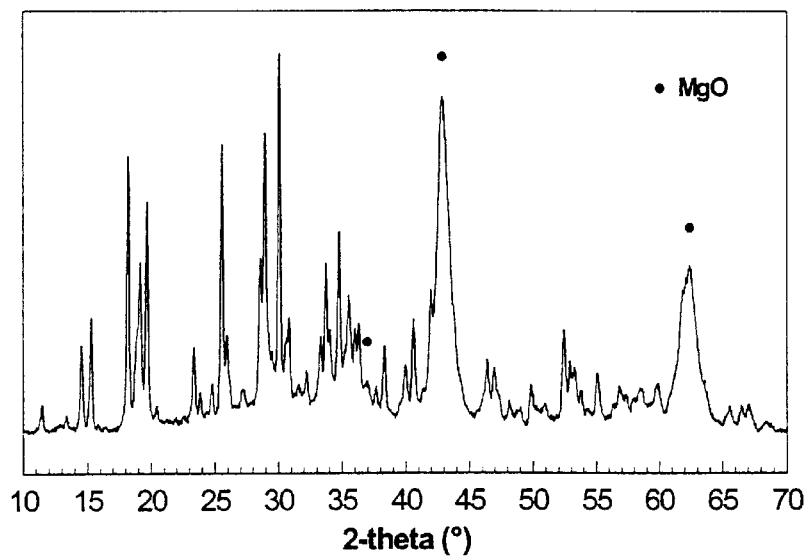

X-ray diffraction spectrum of the new Bi/V/Mg/O crystalline phase in admixture with MgO

Fig.7.1.a
EB Conversion %
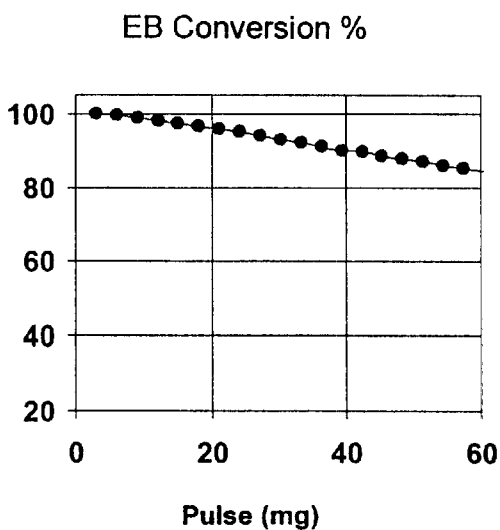
Pulse (mg)
Fig.7.1.b
Selectivity % to STY
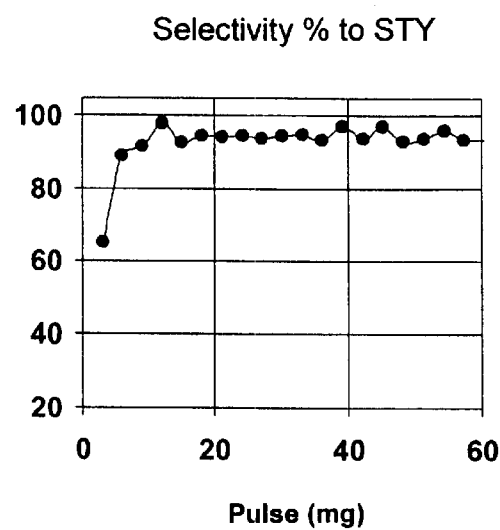
Pulse (mg)
Fig.7.2.a
EB Conversion %
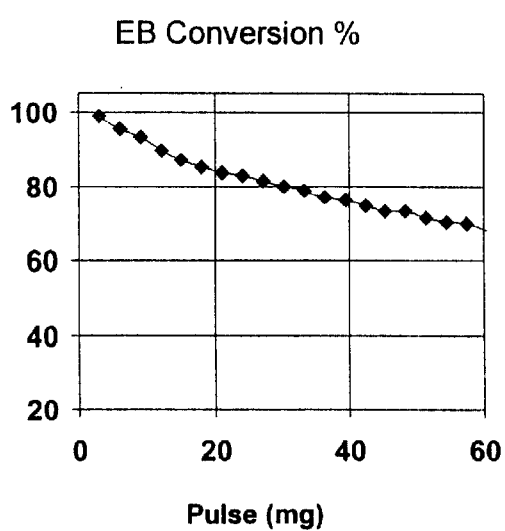
Pulse (mg)
Fig.7.2.b
Selectivity % to STY
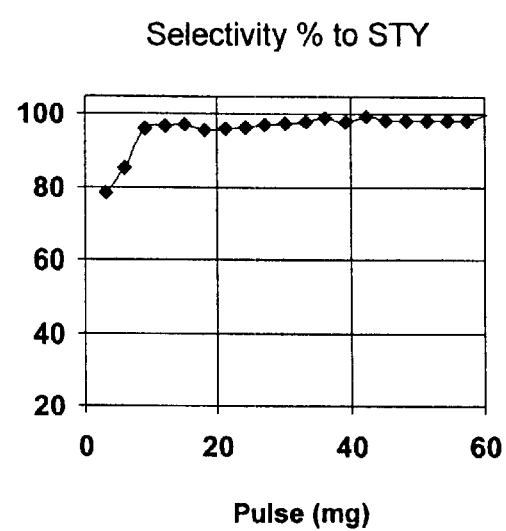
Pulse (mg)

Fig.7.3.a
EB Conversion %
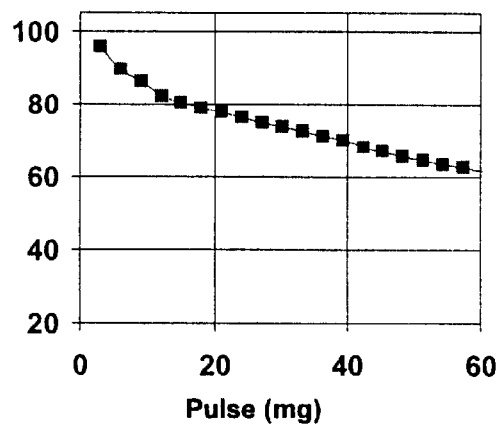
Fig.7.3.b
Selectivity % to STY
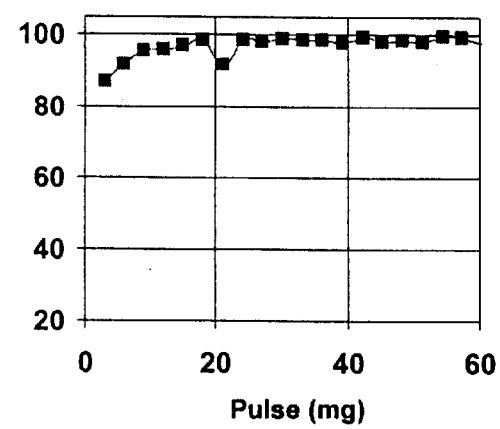
Fig.7.4.a
EB Conversion %
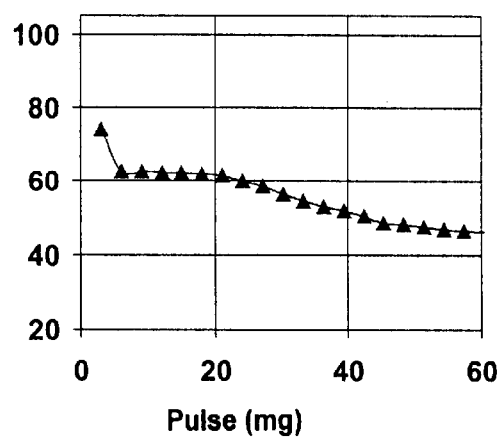
Fig.7.4.b
Selectivity % to STY
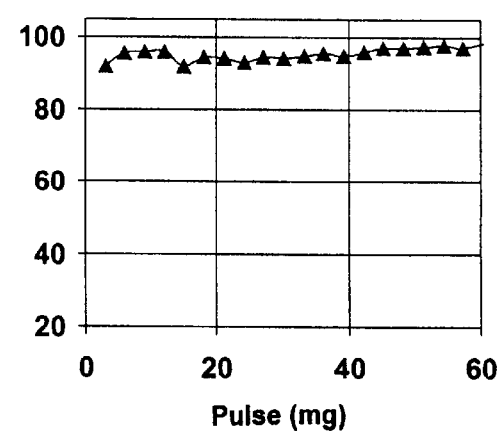

Fig.8.1.a
EB Conversion %
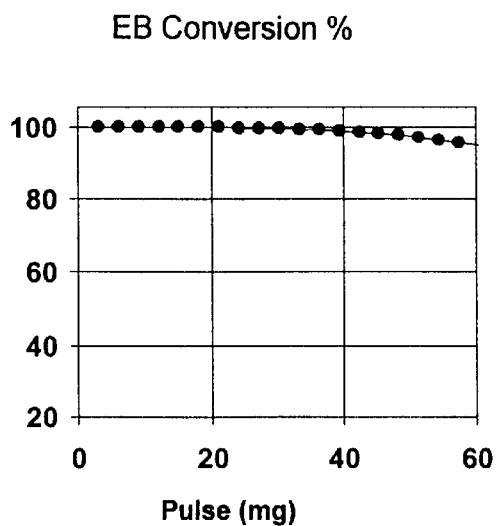
Pulse (mg)
Fig.8.1.b
Selectivity % to STY
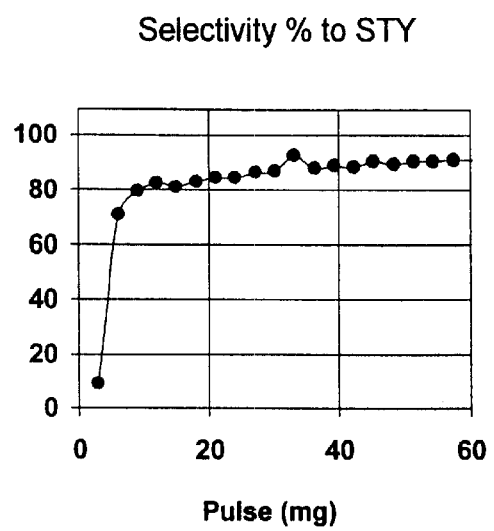
Pulse (mg)
Fig.8.2.a
EB Conversion %
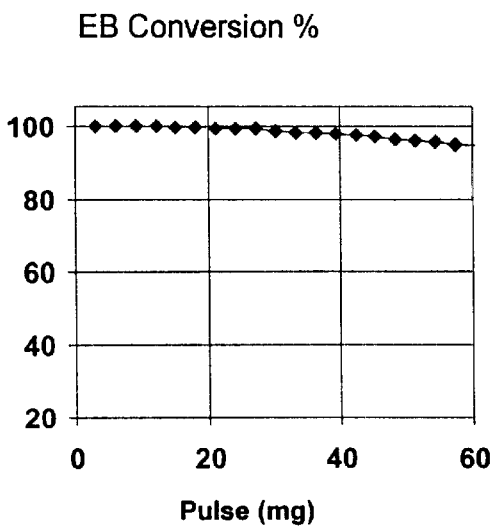
Pulse (mg)
Fig.8.2.b
Selectivity % to STY
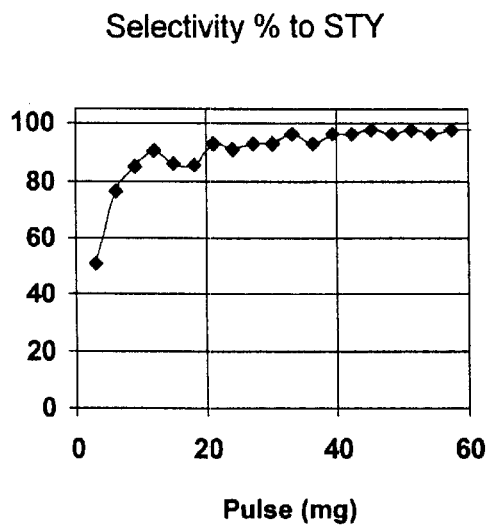
Pulse (mg)

Fig.8.3.a
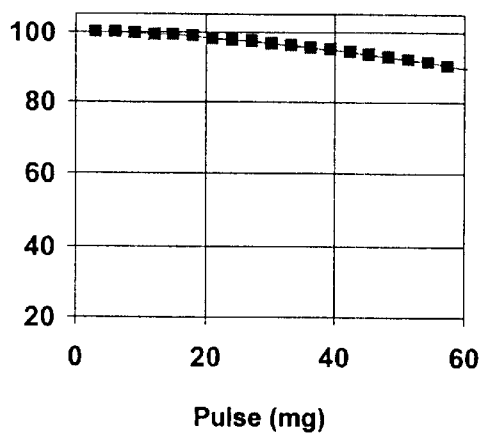
EB Conversion %
Fig.8.3.b
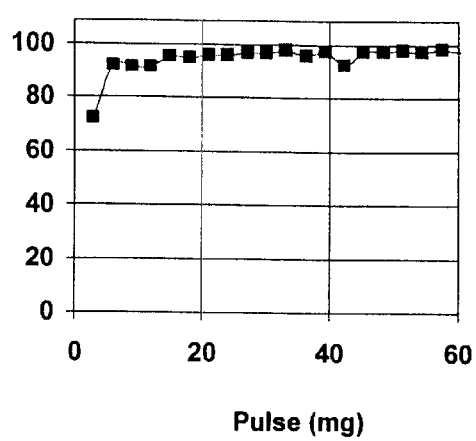
Selectivity % to STY
Fig.8.4.a
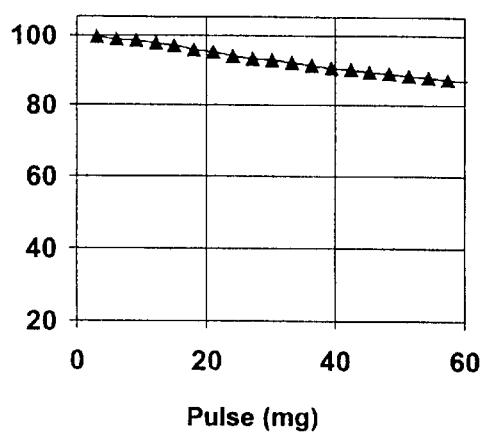
EB Conversion %
Fig.8.4.b
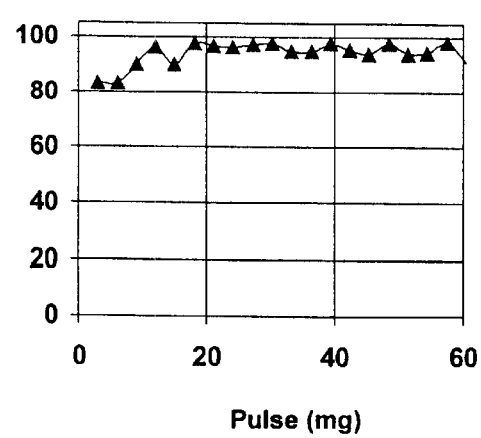
Selectivity % to STY

Fig.9.1.a
EB Conversion %
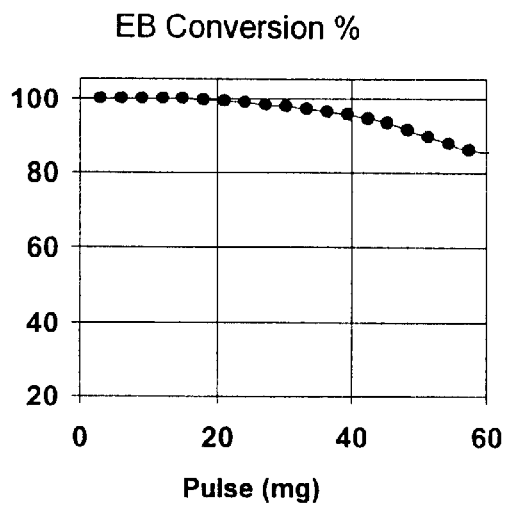
Fig.9.1.b
Selectivity % to STY
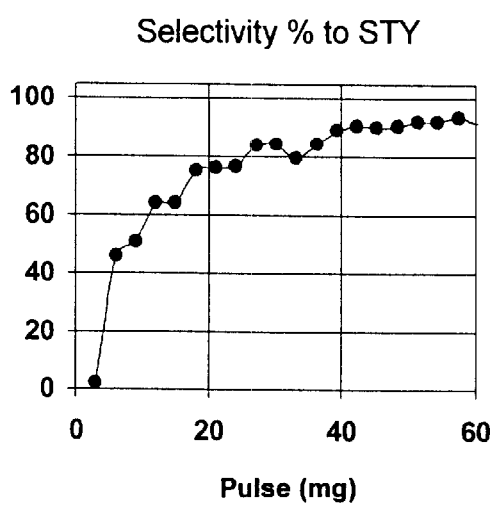
Fig.9.2.a
EB Conversion %
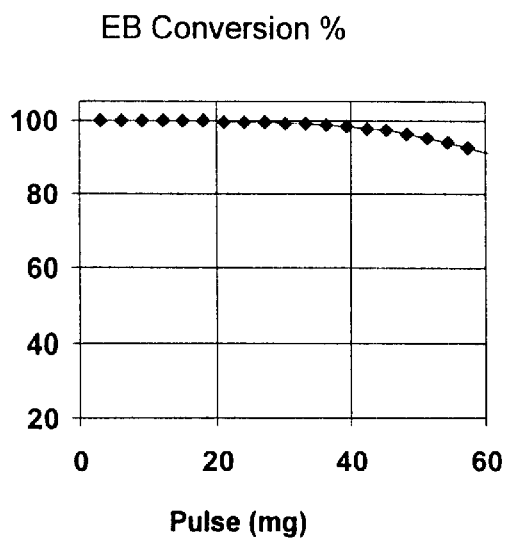
Fig.9.2.b
Selectivity % to STY
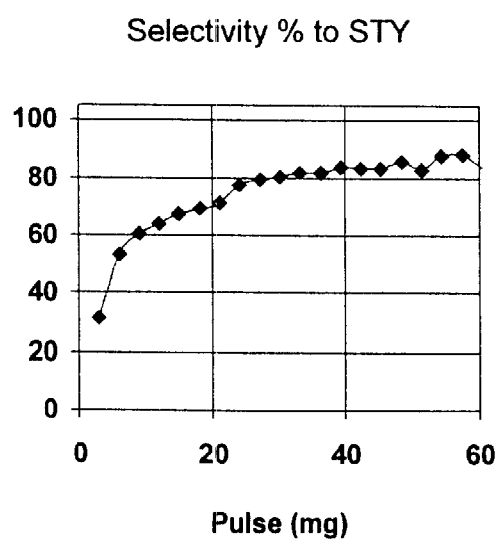

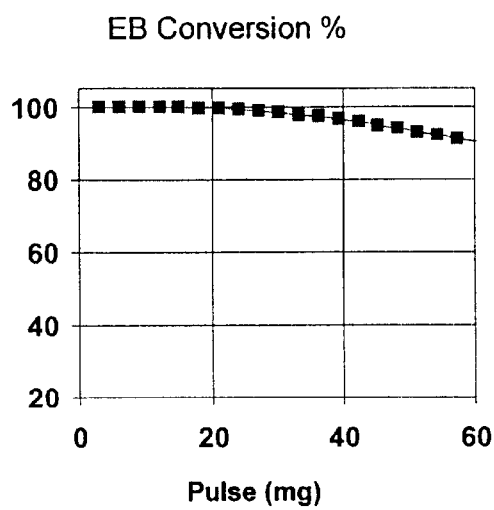
Fig.9.3.a
EB Conversion %
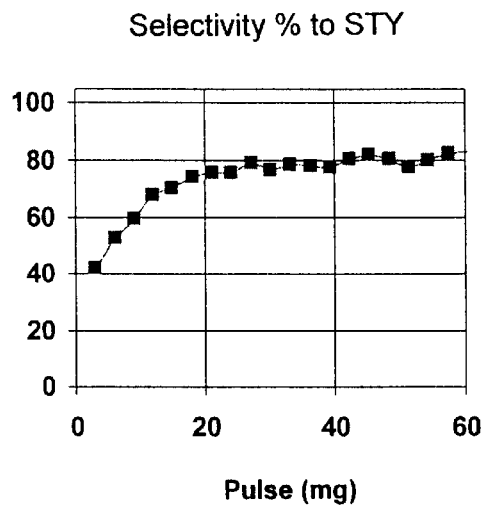
Fig.9.3.b
Selectivity % to STY
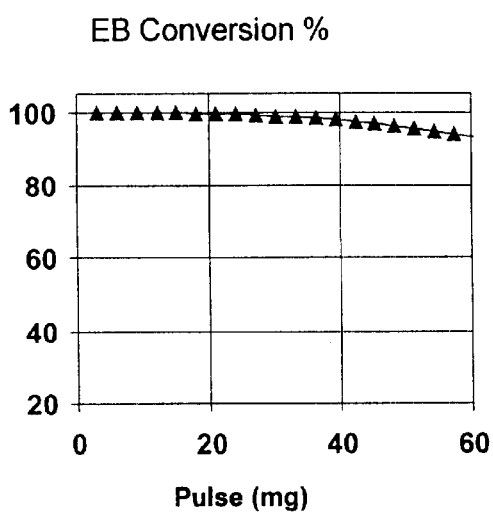
Fig.9.4.a
EB Conversion %
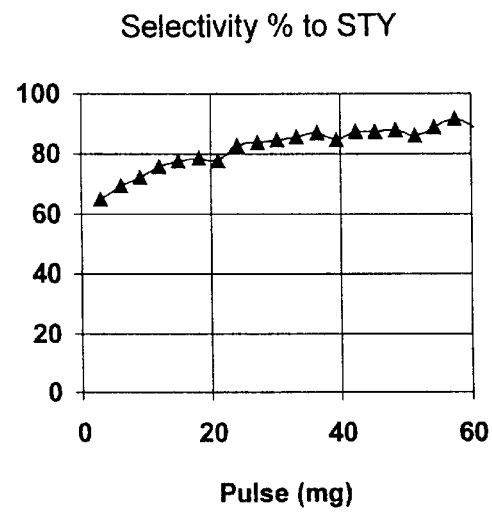
Fig.9.4.b
Selectivity % to STY

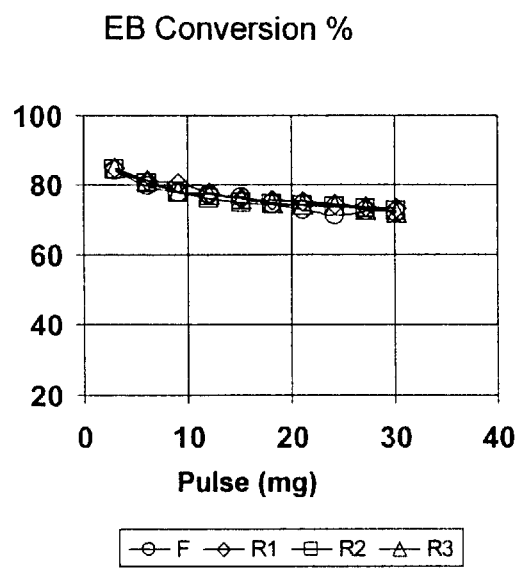
Fig.10.a
EB Conversion %
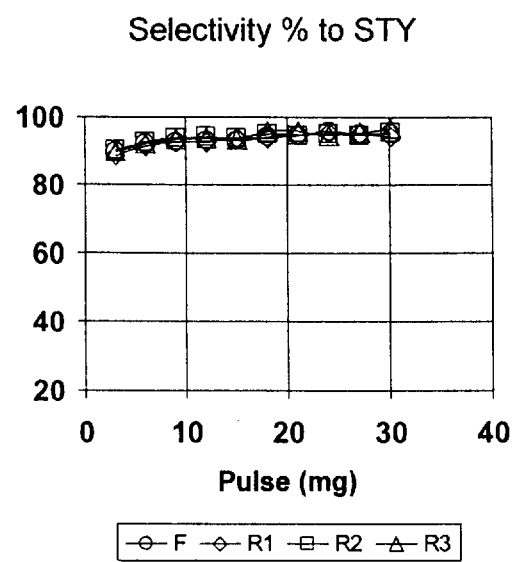
Fig.10.b
Selectivity % to STY

PROCESS FOR THE PREPARATION OF CATALYTIC SYSTEMS FOR THE OXIDATIVE DEHYDROGENATION OF ALKYLAROMATICS OR PARAFFINS

The present invention relates to a process for the preparation of catalytic systems for the oxidative dehydrogenation of alkylaromatics, in particular ethylbenzene, to the corresponding alkenylaromatics, in particular styrene, or of paraffins to the corresponding olefins.

Styrene, which is an important intermediate for the production of plastic materials, is mainly used in the production of polystyrenes (crystal GPPS, high impact HIPS and expandable EPS), acrylonitrile-styrene-butadiene (ABS) and styrene-acrylonitrile (SAN) copolymers, and styrene-butadiene rubbers (SBR).

Styrene is currently produced mainly by means of two processes: by the dehydrogenation of ethylbenzene (EB) and, as co-product, in the epoxidation of propylene with ethylbenzene hydroperoxide with catalysts based on molybdenum complexes.

An alternative method for the production of the monomer is the dehydrogenation of ethylbenzene with the contemporaneous oxidation of hydrogen which can be carried out in the presence or in the absence of oxygen.

Oxidative dehydrogenation in the absence of oxygen consists in the use of one or more metallic oxides which, in addition to catalyzing the dehydrogenation reaction of ethylbenzene, is capable of oxidizing the hydrogen produced, by means of the oxygen available in the oxide itself, in order to favour the equilibrium shift towards the formation of styrene (STY) by means of the following reaction

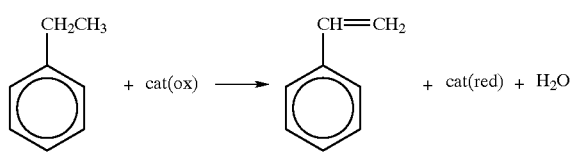

(1)

It can be seen from reaction (1) that the catalyst also participates in the reaction stoichiometry, acting as reagent: at the beginning of the reaction, it is in an oxidized state ($cat_{ox}$) capable of releasing part of its oxygen and becoming transformed into a reduced species ($cat_{red}$). In order to make the reaction catalytic, the reduced catalyst must be able to easily re-acquire oxygen to be transformed into the starting oxidized species, which can be used for a new oxidative dehydrogenation cycle, by means of the following reaction:

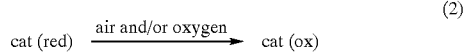

(2)

This particular way of carrying out dehydrogenation offers the same advantages as traditional oxidative dehydrogenation, i.e. in the presence of oxygen, allowing the necessary heat supply for the dehydrogenation and the equilibrium shift of the dehydrogenation reaction towards the products.

The idea of effecting the oxidative dehydrogenation of hydrocarbons in the absence of an oxidizing gas was already known and described in the first half of the sixties' by U.S. Pat. No. 3,118,007 of Bayer. This patent claims a process for the dehydrogenation of hydrocarbons in the absence of oxidizing gases and with catalysts based on iron oxides which also act as oxygen carriers. The possibility of operating under fluid bed conditions in order to be able to continuously remove the catalyst to be subjected to a re-oxidation phase and then recycled to the reaction phase, is also described.

Various patents have been filed in the last few years again relating to oxidative dehydrogenation without oxidizing gases of which the most significant are the following.

EP-482276 of FINA describes a process whereby a total conversion of ethylbenzene is obtained already at 505° C. With a catalyst, acting as oxygen carrier, which, once exhausted, can be regenerated in a second reactor by treatment with air. The catalyst, containing transition metal oxides, preferably based on vanadium supported on magnesium, has a high dehydrogenating activity as well as a strong tendency to release structural oxygen by the combustion of hydrogen. The results indicated in this patent show that combustion is the most critical phase of the reaction: at the beginning of the catalytic activity, in fact, styrene is produced with a low selectivity together with a high quantity of carbon oxides deriving from the combustion of ethylbenzene and/or styrene. In the same patent, it is shown that a partial pre-reduction of the catalyst, by treatment with carbon monoxide, allows its high oxidizing capacity to be moderated, obtaining high selectivities to styrene already in the first phases of activity. In this case however the conversion drops rapidly and becomes stable in a short time at values around 50%.

GB-2297043 of BASF claims the use of a catalyst consisting of a mixed oxide based on bismuth, titanium, lanthanum, potassium and treated with a noble metal, for the oxidative dehydrogenation of ethylbenzene in the absence of oxygen. The results indicated do not allow the catalytic performances over a period of time to be accurately evaluated. The patent text discloses that the catalyst is initially extremely active but has a low selectivity with the formation of compounds deriving from the combustion of hydrocarbons. As already observed in the case of the FINA patent, as the reaction proceeds, the catalyst becomes less active and more and more selective until it reaches a maximum value.

The same applicants have recently filed a patent application (IT-MI99A001242) which describes a catalytic system consisting of:
a vanadium oxide;
a bismuth oxide;
and a carrier based on magnesium,
wherein the vanadium, expressed as $V_2O_5$, is in a quantity ranging from 1 to 15% by weight, preferably from 2 to 10%, the bismuth, expressed as $Bi_2O_3$, ranges from 2 to 30% by weight, preferably from 5 to 25% by weight,
the complement to 100 being the carrier.
The magnesium-based carrier is preferably selected from:
  carriers consisting of magnesium oxide;
  carriers consisting of magnesium oxide and zirconium oxide;
  carriers consisting of magnesium and aluminum hydrotalcites.

The process for preparing the catalytic system described in the above Italian patent application can be essentially carried out by means of the following steps:
  preparation of the solutions or suspensions based on derivatives of the components of the catalytic system;
  mixing of the solutions or suspensions prepared until gelation of the mixture;
  drying of the gel obtained;

calcination of the dried solid at a temperature ranging from 550 to 780° C.

We have now found a different preparation process for obtaining the catalytic system described above, which can be used when the carrier consists of magnesium oxide.

The catalytic system thus obtained, with respect to the known catalysts described above, not only provides better selectivity characteristics, above all at the beginning of the reaction, and obtains a higher total productivity, but also has a longer life duration.

The process, object of the present invention, for preparing catalytic systems consisting of:
a vanadium oxide;
a bismuth oxide;
and a carrier consisting of magnesium oxide,
wherein the vanadium, expressed as $V_2O_5$, is in a quantity ranging from 2 to 35% by weight,
the bismuth expressed as $Bi_2O_3$, ranges from 2 to 40% by weight,
the complement to 100 being the carrier, is characterized in that it essentially comprises the following steps:
preparation of solutions based on derivatives of the components of the catalytic system;
mixing of the solutions prepared and optional aging;
drying of the solution obtained;
first heating, in the presence of air, of the solid obtained from the drying at a temperature ranging from room value to a temperature of between 290 and 310° C., for a time ranging from 1 to 3 hours;
optional second heating, in the presence of air, of the solid for a time ranging from 0.5 to 2 hours at a constant temperature, ranging from 290 to 310° C., reached in the first heating;
additional heating, in the presence of air, of the solid for a time ranging from 2 to 4 hours at the calcination temperature ranging from 600 to 850° C.;
calcination, in the presence of air, of the solid at a constant temperature, ranging from 600 to 850° C., reached in the additional heating, for a time ranging from 8 to 16 hours.

The catalytic system obtained in accordance with the invention, in its calcined form at a temperature ranging from 600° C. to 850° C., has an X-ray diffraction spectrum, registered by means of a vertical goniometer equipped with an electronic diffracted radiation count system and using copper Kα radiation (wave length=1,5418 Å), of the type indicated in FIGS. 1–6, containing reflections whose interplanar distance values are indicated in Table 2.

The catalytic system is characterized by the presence of at least two of the following three phases:
the ever present MgO crystalline phase;
the new Bi/Mg/V/O crystalline phase (with an unknown structure),
the $BiMg_2VO_6$ crystalline phase.

The relative quantity of Bi/Mg/V/O and $BiMg_2VO_6$ crystalline phases is determined not only by the chemical composition, but also by the temperature and calcination procedure.

In particular:
on effecting the calcination at a temperature ranging from 600 to 800° C., a catalytic system is obtained, characterized by a Bi/Mg/V/O crystalline phase, with an X-ray diffraction spectrum as indicated in Table 1, ranging from 10 to 45%, an MgO crystalline phase and a $BiMg_2VO_6$ crystalline phase, which is sometimes not present.

on effecting the calcination at a temperature higher than 800° C. and lower than or equal to 850° C., a catalytic system is obtained, characterized by an MgO crystalline phase and a $BiMg_2VO_6$ crystalline phase.

In the case of a calcination carried out at 600 to 800° C., it can be observed that the catalytic system is characterized by the presence (FIGS. 1–5, Table 2) of an MgO crystalline phase, a new Bi/Mg/V/O crystalline phase (with an unknown structure), with an X-ray diffraction spectrum as indicated in Table 1, and the $BiMg_2VO_6$ crystalline phase which is sometimes not present (FIG. 1). Other crystalline phases such as (for example): $Mg_3V_2O_8$, $Mg(Mg,V)O_4$, etc. may also be occasionally present, in smaller quantities.

Figure 6:
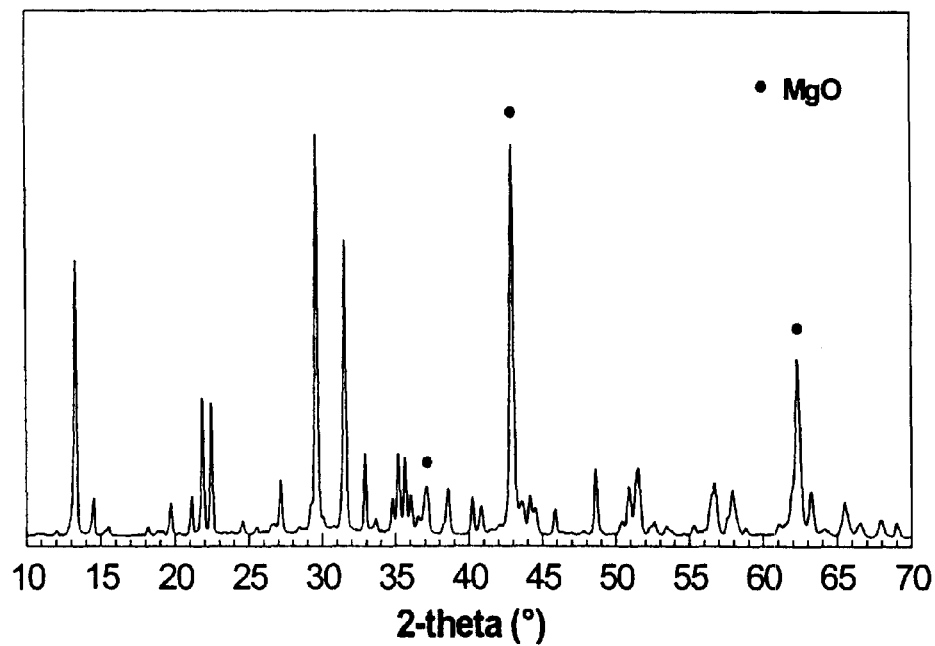

In the case of a calcination carried out at a temperature higher than 800° C. and lower than or equal to 850° C., it can be observed that the catalytic system is characterized by an X-ray diffraction spectrum as illustrated in FIG. 6.

In the catalytic system claimed, the vanadium, expressed as $V_2O_5$, is preferably in a quantity ranging from 5 to 30% by weight, more preferably from 10 to 25%, and the bismuth, expressed as $Bi_2O_3$, preferably ranges from 10 to 20% by weight.

The catalytic system according to the invention can be applied to any dehydrogenation technology of ethylbenzene whether it be fixed, fluid or mobile bed.

The process, further object of the present invention, for the oxidative dehydrogenation of alkylaromatics, in particular ethylbenzene, into the corresponding alkenylaromatics, in particular styrene, or paraffins into the corresponding olefins, substantially consists in reacting the alkylaromatic or paraffin, optionally in the presence of a diluent, in a reactor, operating at a temperature ranging from 350 to 750° C., preferably from 370 to 550° C., at a pressure ranging from 0.1 to 30 psia and with a GHSV space velocity ranging from 0.01 to 10 $sec^{-1}$, preferably from 0.1 to 1 $sec^{-1}$ (normal-liters of hydrocarbon/sec×liter of catalyst), with the catalytic system described above and regenerating said catalytic system in a regenerator by burning the coke deposited during the reaction phase, operating at a temperature higher than 400° C.

The oxidizing medium used in said process can be oxygen and/or air.

The optional diluent can be, for example, $N_2$, $CH_4$, $H_2O_{vapour}$, CO, $CO_2$, etc.

In order to avoid having substantially aldehydes and/or ketones in the products obtained, it is advisable to use charges without oxygenated compounds (in particular peroxides).

Some examples are provided for a better illustration of the present invention without limiting its scope in any way.

EXAMPLES 5 syntheses of catalysts are described followed by the corresponding catalytic tests.

Examples 1–4

Synthesis of the Catalysts

The following solutions are prepared:
solution A: 62.4 g of $Mg(CH_3COO)_2.4H_2O$ (M.W.=214 $gmol^{-1}$, 0.288 mol MgO) are dissolved in 200 g of water
solution B: 5.63 g of $NH_4VO_3$ (M.W.=117 $gmol^{-1}$, 2.40·10$^{-2}$ mol $V_2O_5$) are dissolved in 120 g of water acidified by the addition of 18.4 g of citric acid
solution C: 5.82 g of $Bi(NO_3)_3.5H_2O$ (M.W.=485 $gmol^{-1}$, 6.00·10$^{-3}$ mol $Bi_2O_3$) are dissolved in 20 g of water acidified by the addition of 3.2 g of $HNO_3$ at 65%
Solutions B and C are added in rapid succession, under vigorous stirring, to solution A, obtaining a yellow-greencoloured solution. This solution is left in aging for 1 hour and is then dried by evaporation. The solid is divided into four aliquots.

Example 1
Catalyst 1

The first aliquot is calcined according to the following temperature profile: from 50° C. to 300° C. in two hours, it is left for an hour at a temperature of 300° C., is then heated to 650° C. in three hours and is kept at a temperature of 650° C. for twelve hours.

Figure 2:
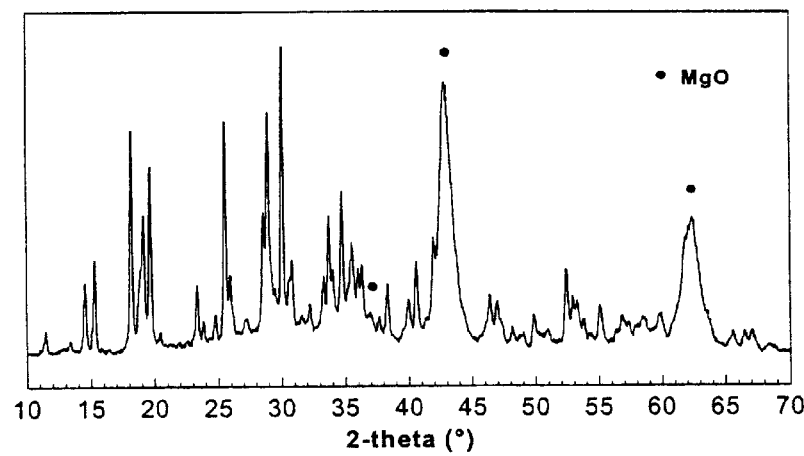

Catalyst 1 has an X-ray diffraction spectrum as shown in FIG. 2 and Table 2.

Example 2
Catalyst 2

The second aliquot is calcined according to the following temperature profile: from 50° C. to 300° C. in two hours, it is left for an hour at a temperature of 300° C., is then heated to 700° C. in three hours and is kept at a temperature of 700° C. for twelve hours.

Figure 3:
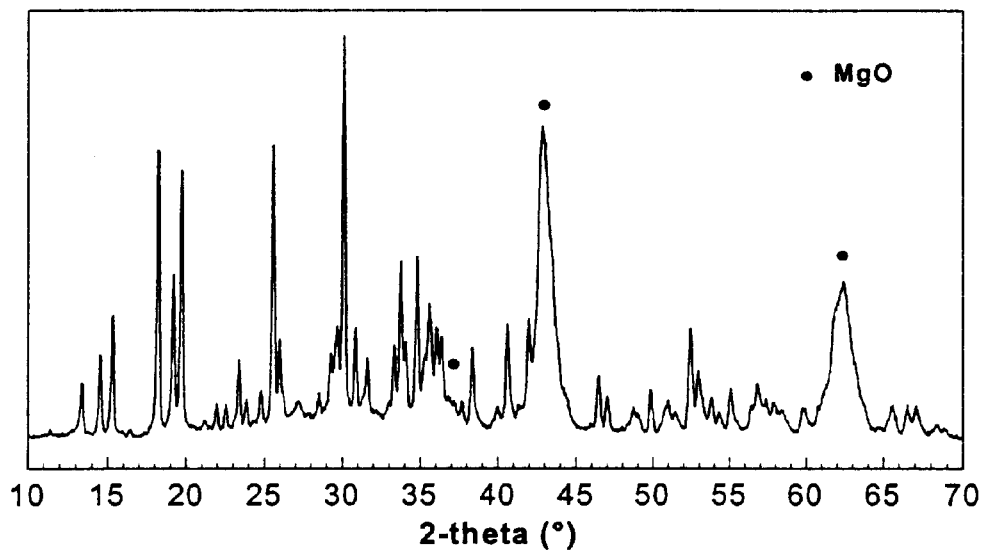

Catalyst 2 has an X-ray diffraction spectrum as shown in FIG. 3 and Table 2.

Example 3
Catalyst 3

The third aliquot is calcined according to the following temperature profile: from 50° C. to 300° C. in two hours, it is left for an hour at a temperature of 300° C., is then heated to 750° C. in three hours and is kept at a temperature of 750° C. for twelve hours.

Figure 4:
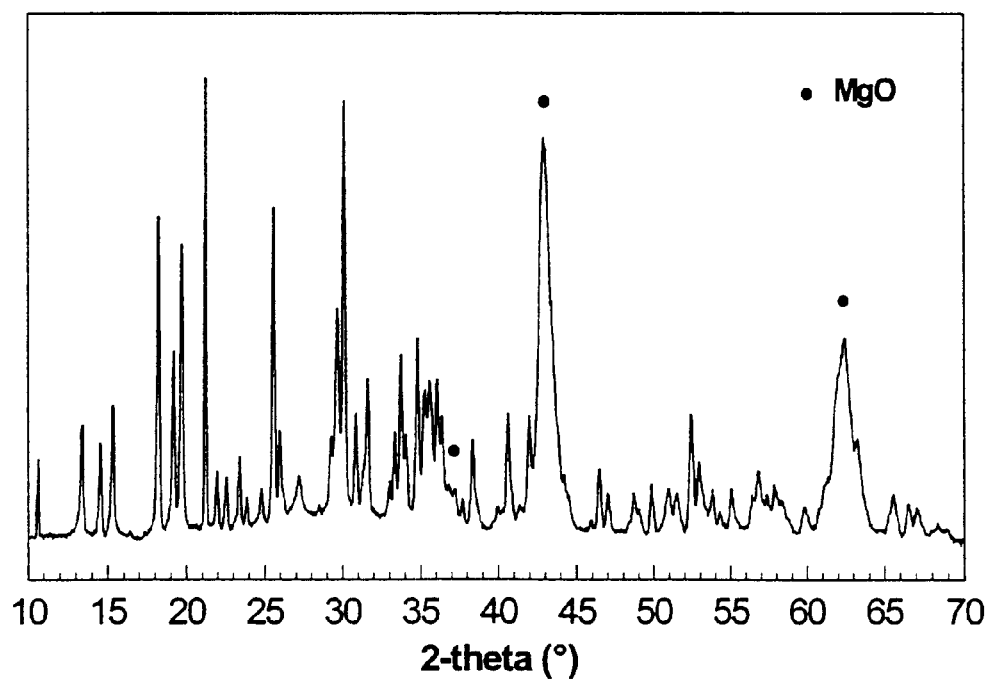

Catalyst 3 has an X-ray diffraction spectrum as shown in FIG. 4 and Table 2.

Example 4
Catalyst 4

The fourth aliquot is calcined according to the following temperature profile: from 50° C. to 300° C. in two hours, it is left for an hour at a temperature of 300° C., is then heated to 800° C. in three hours and is kept at a temperature of 800° C. for twelve hours.

All the calcination phases are carried out in a stream of air.

Figure 5:
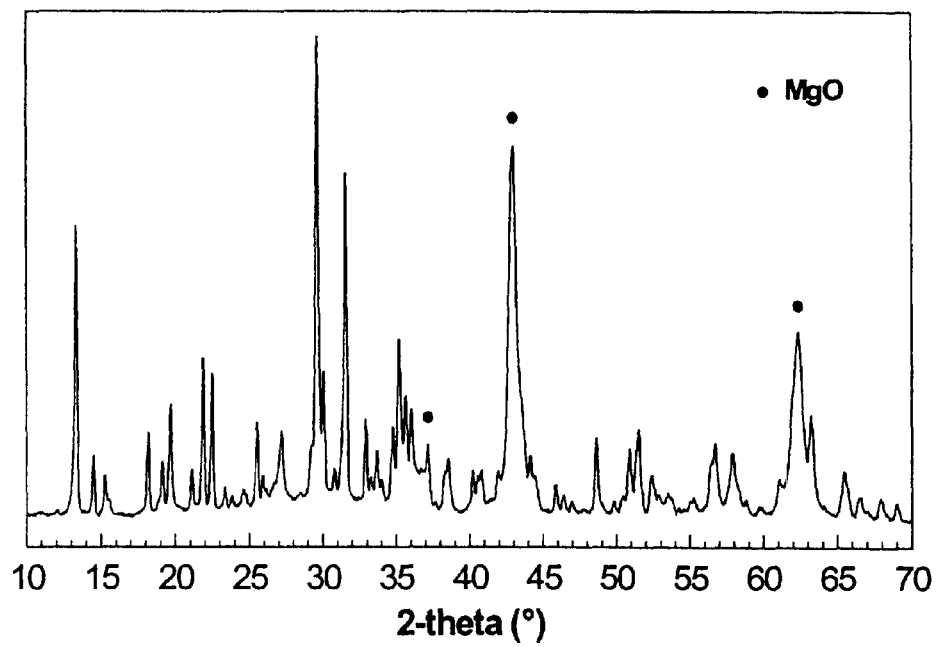

Catalyst 4 has an X-ray diffraction spectrum as shown in FIG. 5 and Table 2.

Example 5
Catalyst 5

The following solutions are prepared:

solution A: 62.4 g of $Mg(CH_3COO)_2 \cdot 4H_2O$ (M.W.=214 $gmol^{-1}$, 0.288 mol MgO) are dissolved in 200 g of water solution B: 4.22 g of $NH_4VO_3$ (M.W.=117 $gmol^{-1}$, $1.80 \cdot 10^{-2}$ mol $V_2O_5$) are dissolved in 120 g of water acidified by the addition of 13.8 g of citric acid solution C: 5.82 g of $Bi(NO_3)_3 \cdot 5H_2O$ (M.W.=485 $gmol^{-1}$, $6.00 \cdot 10^{-3}$ mol $Bi_2O_3$) are dissolved in 20 g of water acidified by the addition of 3.2 g of $HNO_3$ at 65%

Solutions B and C are added in rapid succession, under vigorous stirring, to solution A, obtaining a yellow-green-coloured solution. This solution is left to rest for 1 hour and is then dried by evaporation. The solid is calcined according to the following temperature profile: from 50° C. to 300° C. in two hours, it is left for an hour at a temperature of 300° C., is then heated to 850° C. in three hours and is kept at a temperature of 850° C. for twelve hours. All the calcination phases are carried out in a stream of air.

Catalyst 5 has an X-ray diffraction spectrum as shown in FIG. 6.

Example 6
Synthesis of Catalyst 6

The following solutions are prepared:

solution A: 62.40 g of $Mg(CH_3COO)_2 \cdot 4H_2O$ (M.W.=214 $gmol^{-1}$, 0.288 mol MgO) are dissolved in 200 g of water solution B: 4.22 g of $NH_4VO_3$ (M.W.=117 $gmol^{-1}$, $1.80 \cdot 10^{-2}$ mol $V_2O_5$) are dissolved in 120 g of water acidified by the addition of 13.80 g of citric acid solution C: 5.82 g of $Bi(NO_3)_3 \cdot 5H_2O$ (M.W.=485 $gmol^{-1}$, $6.00 \cdot 10^{-3}$ mol $Bi_2O_3$) are dissolved in 20 g of water acidified by the addition of 3.2 g of $HNO_3$ at 65%

Solutions B and C are added in rapid succession, under vigorous stirring, to solution A, obtaining a yellow-green-coloured suspension. This suspension is dried by evaporation and calcined according to the following temperature profile: from 50° C. to 300° C. in two hours, it is left for an hour at a temperature of 300° C., is then heated to 750° C. in three hours and is kept at a temperature of 750° C. for twelve hours. All the calcination phases are carried out in a stream of air.

Catalyst 6 has an X-ray diffraction spectrum as shown in Table 2.

Examples 7–10
Catalytic Test

All the catalytic tests were carried out in a micro-reactor with the pulse feeding of ethylbenzene. In all the tests, 500 mg of catalyst were charged, which were activated in an atmosphere of air at 500° C. for 2 hours. At the end of this pretreatment, the reactions were effected at 375° C., by feeding pulses of ethylbenzene of about 3 mg, with a contact time of about 1.1 sec.

The conversions of ethylbenzene and selectivities to styrene are indicated in the graphs of FIGS. 7.1*a*–7.4*a* and 7.1*b*–7.4*b* respectively (wherein the number following "7" refers to the synthesis example of the catalyst used).

Examples 11–14
Catalytic Test

All the catalytic tests were carried out in a micro-reactor with the pulse feeding of ethylbenzene. In all the tests, 500 mg of catalyst were charged, which were activated in an atmosphere of air at 500° C. for 2 hours. At the end of this pretreatment, the reactions were effected at 450° C., by feeding pulses of ethylbenzene of about 3 mg, with a contact time of about 1.1 sec.

The conversions of ethylbenzene and selectivities to styrene are indicated in the graphs of FIGS. 8.1*a*–8.4*a* and 8.1*b*–8.4*b* respectively (wherein the number following "8" refers to the synthesis example of the catalyst used).

Examples 15–18
Catalytic Test

All the catalytic tests were carried out in a micro-reactor with the pulse feeding of ethylbenzene. In all the tests, 500 mg of catalyst were charged, which were activated in an atmosphere of air at 500° C. for 2 hours. At the end of this pretreatment, the reactions were effected at 450° C., by feeding pulses of ethylbenzene of about 3 mg, with a contact time of about 1.1 sec.

The conversions of ethylbenzene and selectivities to styrene are indicated in the graphs of FIGS. 9.1*a*–9.4*a* and 9.1*b*–9.4*b* respectively (wherein the number following "9" refers to the synthesis example of the catalyst used).

Example 19

Regeneration Test atalyst 6, at the end of the test, was regenerated in air at 500° C. for 2 hours. At the end of this treatment, it was subjected to another catalytic test according to what is described in examples 7–10. The same procedure was repeated a further two times.

The conversions of ethylbenzene and selectivities to styrene are indicated in the graphs of FIGS. 10.$a$ and 10.$b$ respectively (wherein the curve F indicates the performance of the fresh catalyst and R, R2, R3 the performances of the catalyst after the 1$^{st}$, 2$^{nd}$ and 3$^{rd}$ regeneration, respectively).

TABLE 1

X-ray diffraction spectrum of the new Bi/Mg/V/O crystalline phase.

| Interplanar distance $d_{hkl}$ (Å) | Relative intensity (arbitrary units) |
|---|---|
| 7.71 | 17 |
| 6.62 | 14 |
| 6.09 | 31 |
| 5.78 | 37 |
| 4.867 | 76 |
| 4.631 | 51 |
| 4.506 | 65 |
| 4.342 | 16 |
| 3.805 | 30 |
| 3.725 | 19 |
| 3.589 | 21 |
| 3.482 | 78 |
| 3.430 | 33 |
| 3.281 | 20 |
| 3.121 | 51 |
| 3.081 | 81 |
| 2.969 | 100 |
| 2.898 | 37 |
| 2.775 | 24 |
| 2.688 | 32 |
| 2.654 | 50 |
| 2.632 | 34 |
| 2.578 | 58 |
| 2.524 | 43 |
| 2.491 | 35 |
| 2.470 | 36 |
| 2.386 | 21 |
| 2.348 | 30 |
| 2.254 | 26 |
| 2.221 | 37 |
| 2.151 | 44 |
| 1.955 | 27 |
| 1.933 | 25 |
| 1.889 | 17 |
| 1.828 | 21 |
| 1.792 | 17 |
| 1.744 | 34 |
| 1.729 | 27 |
| 1.718 | 20 |
| 1.704 | 24 |
| 1.667 | 17 |
| 1.632 | 21 |
| 1.619 | 19 |
| 1.607 | 18 |
| 1.588 | 20 |
| 1.576 | 20 |

TABLE 2

X-ray spectrum of a polyphasic sample (some weak lines have been omitted)

| Interplanar distance $d_{hkl}$ (Å) | Bi/Mg/V/O | BiMg$_2$VO$_6$ | MgO |
|---|---|---|---|
| 6.63 | X | X | |
| 6.11 | X | X | |
| 5.79 | X | | |
| 4.867 | X | | |
| 4.631 | X | | |
| 4.506 | X | | |
| 4.203 | | X | |
| 4.057 | | X | |
| 3.951 | | X | |
| 3.805 | X | | |
| 3.627 | | X | |
| 3.482 | X | | |
| 3.430 | X | | |
| 3.281 | X | | |
| 3.012 | X | X | |
| 2.969 | X | | |
| 2.898 | X | | |
| 2.832 | | X | |
| 2.718 | | X | |
| 2.654 | X | | |
| 2.579 | X | X | |
| 2.516 | | X | |
| 2.491 | X | | |
| 2.419 | | | X |
| 2.333 | X | X | |
| 2.240 | X | X | |
| 2.210 | X | X | |
| 2.152 | X | | |
| 2.104 | | | X |
| 2.051 | | X | |
| 1.977 | | X | |
| 1.956 | X | | |
| 1.871 | | X | |
| 1.793 | | X | |
| 1.773 | | X | |
| 1.745 | X | | |
| 1.622 | X | X | |
| 1.592 | | X | |
| 1.516 | X | | |
| 1.488 | | | X |
| 1.469 | X | | |
| 1.425 | | X | |
| 1.405 | X | | |

What is claimed is:

1. A process for preparing a catalytic system wherein the catalytic system consists of:
    a vanadium oxide;
    a bismuth oxide;
    and a carrier consisting of magnesium oxide,
    wherein the vanadium, expressed as V$_2$O$_5$, is in a quantity ranging from 2 to 35% by weight,
    the bismuth, expressed as Bi$_2$O$_3$, ranges from 2 to 40% by weight,
    the complement to 100 being the carrier,
    comprising:
        preparing solutions based on derivatives of the components of the catalytic system;
        mixing the prepared solutions and optionally aging;
        drying the solution to obtain a solid;
        first heating the solid in the presence of air from room temperature to a temperature of between 290 and 310° C., for a time ranging from 1 to 3 hours;
        additionally heating the solid in the presence of air for a time ranging from 2 to 4 hours from the temperature reached in the first heating to a calcination temperature ranging from 600 to 850° C.;
        calcining the solid in the presence of air at a constant temperature, ranging from 600 to 850° C., reached in the additional heating, for a time ranging from 8 to 16 hours.

2. The process of claim 1, further comprising heating the solid in the presence of air for a time ranging from 0.5 to 2 hours at a constant temperature, ranging from 290 to 310° C., immediately following the first heating.

3. A catalytic system for the oxidative dehydrogenation of alkylaromatics or paraffins to the corresponding alkenylaromatics or to the corresponding olefins consisting of:

a vanadium oxide;

a bismuth oxide;

and a carrier consisting of magnesium oxide, wherein the vanadium, expressed as $V_2O_5$, is in a quantity ranging from 2 to 35% by weight, the bismuth, expressed as $Bi_2O_3$, ranges from 2 to 40% by weight, the complement to 100 being the carrier, prepared by the process according to claim 1, wherein the calcination temperature ranges from 600 to 800° C., wherein the catalytic system is characterized as containing (I) a Bi/Mg/V/O crystalline phase, with an X-ray diffraction spectrum as indicated in Table 1, ranging from 10 to 45% and an MgO crystalline phase or (II) a Bi/Mg/V/O crystalline phase, with an X-ray diffraction spectrum as indicated in Table 1, ranging from 10 to 45%, an MqO crystalline phase, and a $BiMg_2VO_6$ crystalline phase.

4. A catalytic system for the oxidative dehydrogenation of alkylaromatics or paraffins to the corresponding alkenylaromatics or to the corresponding olefins consisting of:

a vanadium oxide;

a bismuth oxide;

and a carrier consisting of magnesium oxide, wherein the vanadium, expressed as $V_2O_5$, is in a quantity ranging from 2 to 35% by weight, the bismuth, expressed as $Bi_2O_3$, ranges from 2 to 40% by weight, the complement to 100 being the carrier, prepared by the process according to claim 1, wherein the calcination temperature is higher than 800° C. and lower than or equal to 850° C., characterized by an MgO crystalline phase and a $BiMg_2VO_6$ crystalline phase.

5. A catalytic system for the oxidative dehydrogenation of alkylaromatics or paraffins to the corresponding alkenylaromatics or to the corresponding olefins consisting of:

a vanadium oxide;

a bismuth oxide;

and a carrier consisting of magnesium oxide, wherein the vanadium, expressed as $V_2O_5$, is in a quantity ranging from 1 to 15% by weight, the bismuth, expressed as $Bi_2O_3$, ranges from 2 to 30% by weight, the complement to 100 being the carrier, prepared by the process according to claim 1;

wherein the catalytic system is characterized as containing (I) a Bi/Mg/V/O crystalline phase and an MgO crystalline phase or (II) a Bi/Mg/V/O crystalline phase, an MgO crystalline phase and a $BiMg_2VO_6$ crystalline phase, with an X-ray diffraction spectrum as indicated in Tables 1 or 2.

6. A catalytic system for the oxidative dehydrogenation of alkylaromatics or paraffins to the corresponding alkenylaromatics or to the corresponding olefins consisting of:

a vanadium oxide;

a bismuth oxide;

and a carrier consisting of magnesium oxide, wherein the vanadium, expressed as $V_2O_5$, is in a quantity ranging from 1 to 15% by weight, the bismuth, expressed as $Bi_2O_3$, ranges from 2 to 30% by weight, the complement to 100 being the carrier, prepared by the process of claim 1, wherein the catalytic system has an MgO crystalline phase and a $BiMg_2VO_6$ crystalline phase with an X-ray diffraction spectrum as indicated in FIG. 6.

7. The catalytic system according to claim 4, wherein the calcination temperature is 650° C., wherein the catalytic system has an X-ray diffraction spectrum as indicated in FIG. 2.

8. The catalytic system according to claim 4, wherein the calcination temperature is 700° C., wherein the catalytic system has an X-ray diffraction spectrum as indicated in FIG. 3.

9. The catalytic system according to claim 5, wherein the calcination temperature is 750° C., wherein the catalytic system has an X-ray diffraction spectrum as indicated in FIG. 4.

10. The catalytic system according to claim 5, wherein the calcination temperature is 800° C., wherein the catalytic system has an X-ray diffraction spectrum as indicated in FIG. 5.

11. The catalytic system according to claim 6, wherein the calcination is effected at a temperature higher than 800° C. and lower than or equal to 850° C.

12. The catalytic system according to any of the claims from 2 to 11, wherein the vanadium, expressed as $V_2O_5$, is in a quantity ranging from 5 to 30% by weight, and the bismuth, expressed as $Bi_2O_3$, ranges from 10 to 20% by weight.

13. The catalytic system according claim 10, wherein the vanadium, expressed as $V_2O_5$, ranges from 10 to 25% by weight.

14. A process for the dehydrogenation of alkylaromatics into the corresponding alkenylaromatics or of paraffins into the corresponding olefins, comprising reacting the alkylaromatic or paraffin, in a reactor, operating at a temperature ranging from 350 to 750° C., at a pressure ranging from 0.1 to 30 psia and with a GHSV space velocity ranging from 0.01 to 10 $sec^{-1}$ (normal-liters of hydrocarbon/secxliter of catalyst), with the catalytic system according to any one of claims 2 to 10, and regenerating said catalytic system in a regenerator by burning coke deposited during the reaction, wherein said regeneration operates at a temperature higher than 400° C.

\* \* \* \* \*

UNITED STATES PATENT AND TRADEMARK OFFICE
CERTIFICATE OF CORRECTION

PATENT NO. : 6,531,638 B2
DATED : March 11, 2003
INVENTOR(S) : Ingallina et al.

It is certified that error appears in the above-identified patent and that said Letters Patent is hereby corrected as shown below:

<u>Title page,</u>
Item [30], Foreign Application Priority Data, should read:
-- [30]     Foreign Application Priority Data
    Jun. 1, 2000 (IT) .............................. MI2000A001220 --

Signed and Sealed this

Twenty-fourth Day of June, 2003

JAMES E. ROGAN
*Director of the United States Patent and Trademark Office*